United States Patent
Freudenberger et al.

(10) Patent No.: US 7,315,610 B2
(45) Date of Patent: *Jan. 1, 2008

(54) X-RAY DEVICE THAT EMITS AN X-RAY BEAM WITH A SCANNING-LIKE MOVEMENT

(75) Inventors: Jörg Freudenberger, Eckental (DE); Peter Schardt, Höchstadt A.D. Aisch (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/737,292

(22) Filed: Apr. 19, 2007

(65) Prior Publication Data

US 2007/0183585 A1 Aug. 9, 2007

Related U.S. Application Data

(62) Division of application No. 11/197,273, filed on Aug. 4, 2005.

(30) Foreign Application Priority Data

Aug. 4, 2004 (EP) .................................. 04018504

(51) Int. Cl.
*G21K 5/10* (2006.01)

(52) U.S. Cl. .................. 378/146; 378/37; 378/125; 378/134; 378/193

(58) Field of Classification Search .................. 378/37, 378/62, 119, 125, 134, 136, 143, 144, 146, 378/147, 150–152, 193, 196, 197
See application file for complete search history.

(56) References Cited

U.S. PATENT DOCUMENTS

| | | | |
|---|---|---|---|
| 4,685,118 A | 8/1987 | Furbee et al. | 378/114 |
| 4,845,731 A * | 7/1989 | Vidmar et al. | 378/98 |
| 4,928,297 A | 5/1990 | Tsutsui et al. | 378/146 |
| 4,998,270 A | 3/1991 | Scheid et al. | 378/155 |
| 5,544,216 A | 8/1996 | Norhager | 378/149 |
| 5,822,395 A | 10/1998 | Schardt et al. | 378/137 |
| 2004/0202279 A1 | 10/2004 | Besson et al. | 378/37 |
| 2004/0213380 A1 | 10/2004 | Shaw et al. | 378/145 |

FOREIGN PATENT DOCUMENTS

| | | |
|---|---|---|
| DE | 24 27 490 A1 | 1/1975 |
| EP | 0 182 529 | 5/1986 |
| EP | 0 417 965 A2 | 3/1991 |

* cited by examiner

*Primary Examiner*—Jurie Yun
(74) *Attorney, Agent, or Firm*—Schiff Hardin LLP

(57) ABSTRACT

In a method for operating an x-ray device, an x-ray beam is generated at a focal spot of a rotary anode that is rotatable around a rotation axis, and the x-ray beam is gated with a slit-shaped diaphragm to produce a fan-shaped x-ray beam, that is moved through an examination region in the manner of a scan. To improve the image resolution, the fan-shaped x-ray beam can be moved over the examination region essentially in the direction of the rotational axis of the rotary anode by tilting the x-ray tube on the focal spot, with the x-ray tube being tilted on the focal spot so that the fan-shaped x-ray beam is always gated from the region of the overall emitted x-ray beam having the highest image resolution or the highest image definition in the movement through the examination region.

13 Claims, 7 Drawing Sheets

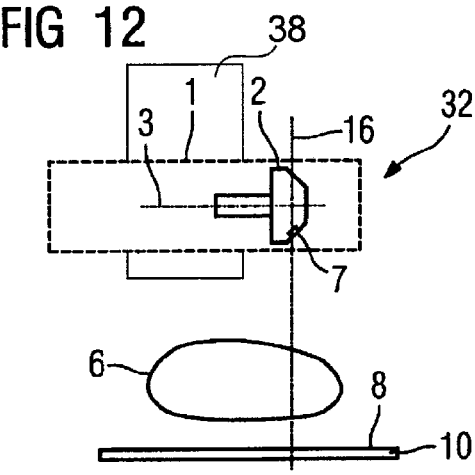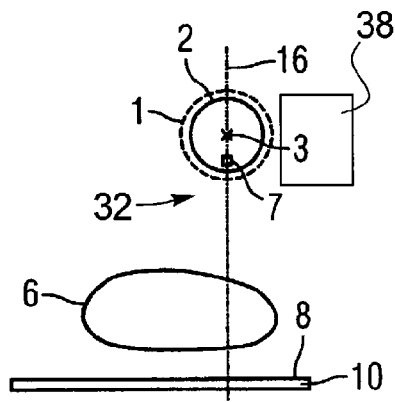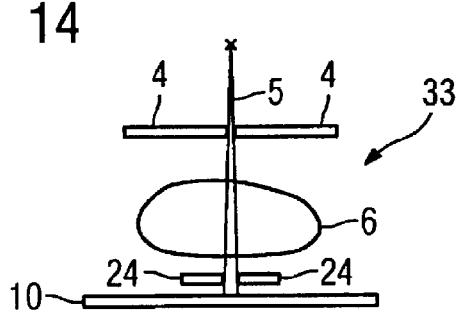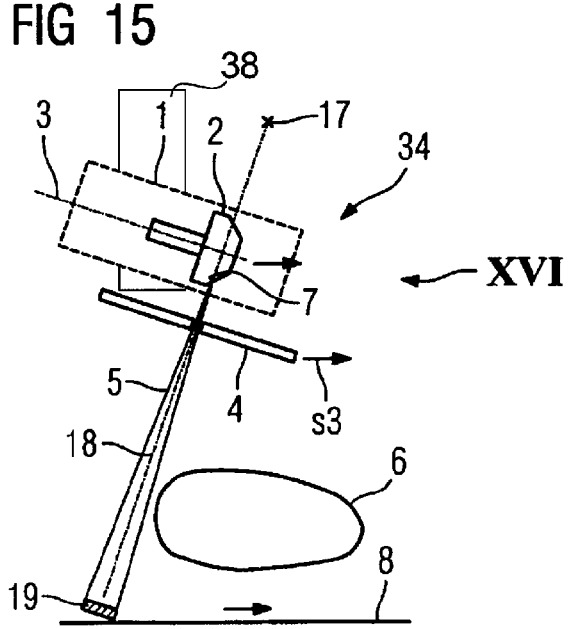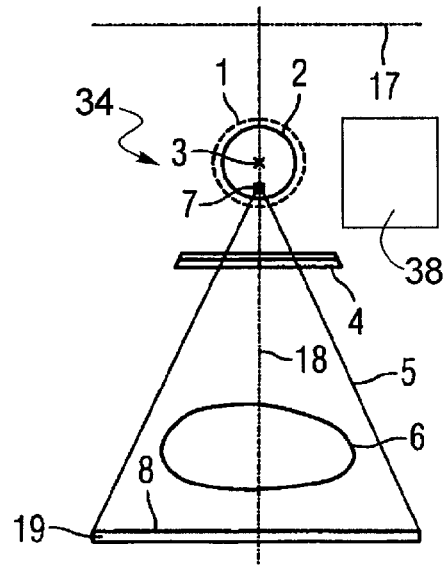

X-RAY DEVICE THAT EMITS AN X-RAY BEAM WITH A SCANNING-LIKE MOVEMENT

RELATED APPLICATION

The present application is a divisional application of copending application Ser. No. 11/197,273, filed Aug. 4, 2005, the teachings of which are incorporated herein by reference.

BACKGROUND OF THE INVENTION

1. Field of the Invention

The present invention concerns a method for operating an x-ray device, in particular a mammography x-ray apparatus, of the type that emits an x-ray beam that exhibits a movement in the manner of a scan of a subject.

2. Description of the Prior Art

In x-ray imaging, the imaging properties are negatively influenced (such as blurring) by the scatter radiation of the x-ray beam generated by an anode, for example a rotary anode. To prevent such scatter radiation, in addition to scattered-ray grids scan methods are used in which a fan-shaped x-ray beam is excised from the totality of emitted, x-rays by a slit-shaped diaphragm, and the diaphragm and the x-ray beam are moved in a grid-like manner over the subject to be imaged. Furthermore, to prevent scatter radiation it is known to provide a further slit diaphragm between the subject and the radiation detector that converts the x-ray radiation into an image signal. It is also known to divide the detector into row-like regions and to only map the respective region passed over by the x-ray beam. It cannot be prevented, however, that regions of the x-ray beam that produce a different image resolution are gated by means of the movement of the diaphragm, such that the generated image exhibits differing image definitions.

An x-ray device for implementing a scanning method is known from U.S. Pat. No. 4,928,297, in which an x-ray tube, a slit-shaped diaphragm and a row-like detector are arranged in a line and are fastened together on a shaft. This unit is mounted such that it can rotate around an axis intersecting the line, above the x-ray tube. The necessary synchronization of the mechanical movements is thereby made particularly simple.

SUMMARY OF THE INVENTION

It is an object of the present invention to provide a method for operating an x-ray device with which an improvement in the quality of x-ray images, in particular with regard to obtaining a sharp image over the entire region, can be achieved in a low-cost manner.

The above object is achieved in accordance with the present invention by a method for operating an x-ray device having an x-ray tube that emits an x-ray beam from a focal spot of a rotary anode that is rotatable around a rotational axis, the emitted x-ray beam having a region that is either a region of highest image resolution or a region of highest image definition. A slit-shaped diaphragm is disposed in the path of the emitted x-ray beam, and gates a fan-shaped x-ray beam therefrom. The fan-shaped x-ray beam is caused to move through an examination region substantially in the direction of the rotational axis of the rotary anode by tilting the x-ray tube relative to the focal spot. The x-ray tube is tilted relative to the focal spot so that the fan-shaped x-ray beam is always gated from the aforementioned region of highest image resolution or region of highest image definition during the movement through the examination region.

The x-ray device is particularly suited for use in a mammography x-ray apparatus.

By tilting the x-ray tube in accordance with the invention with a mounting arrangement for the x-ray tube, the emitted x-ray beam is moved over the examination region so that the fan-shaped beam always is gated from the region of highest image resolution or image sharpness of the emitted x-ray beam (which is on the side of the x-ray beam facing the rotary anode), and thus overall a uniform and high image definition or high image resolution is ensured over the examination region in a simple manner.

The image sharpness can be still further improved in an embodiment wherein, in combination with the tilting of the x-ray tube, the slit-shaped diaphragm can be moved over the examination region substantially in the direction of the rotational axis of the rotary anode and substantially synchronously with the movement of the fan-shaped x-ray beam. This ensures that the region of highest image resolution of the x-ray beam is always gated by the slit-shaped diaphragm.

The use of the inventive x-ray device can be expanded in an advantageous manner by the opening of the slit-shaped diaphragm being adjusted to cover the entire examination region, i.e. in the whole-field range. The x-ray device is thereby made usable for all types of whole-field examinations. The whole-field examination can be still further improved by the inventive x-ray device in an embodiment wherein the slit-shaped diaphragm is adjusted to cover the entire examination region and the x-ray beam is adjusted so its region of highest image resolution stays within this slit solely by the tilting of the x-ray tube in a defined range of the examination region. The tilting of the x-ray tube, which leads to an effective reduction of the anode inclination angle of the rotary anode, also leads to a reduction of the image definition differences over the examination region for a whole-field examination, and thus achieves a sharper image overall. By the tilting of the x-ray tube, the region with the highest image definition can additionally be adjusted to match the subject to be examined, such that a complete utilization of this region is possible.

According to a further embodiment of the invention, the focal spot can be enlarged in the radial direction of the rotary anode. The x-ray power can thereby be increased without loss due to the higher focal spot area, since the tube is inventively tilted to adjust the image definition. The advantage of an increase of the x-ray power is a reduction of the scan time. The shortening of the examination time thereby achieved is desirable for a patient to be examined with the x-ray device since the patient must remain still during the x-ray exposure, which (primarily in mammography) can be painful for the patient.

For variable adjustment (and therewith selectable enlargement as needed) of the focal spot, at least two emitters (in particular of different specifications for generation of a focal spot of corresponding dimensions) are provided in an inventive x-ray device with a cathode for generation of an electron beam. The cathode has at least one emitter with at least one intermediate tap for separate activation of sub-regions of the emitter. The dimensions of the focal spot thus can be increased by using both sub-regions of the emitter. A number of emitters with a number of intermediate taps can also be provided in order to allow further adjustment possibilities of the dimensions of the focal spot.

DESCRIPTION OF THE DRAWINGS

FIG. 12 shows the inventive x-ray device in a side view with an additional first rotation axis.

FIG. 13 is a front view of the inventive x-ray device according to FIG. 12.

FIG. 14 shows the inventive x-ray device in a side view with an additional second rotation axis.

FIG. 15 is a front view of the inventive x-ray device according to FIG. 14.

FIG. 16 shows the inventive x-ray device in a side view with an additional detector-proximate diaphragm.

DESCRIPTION OF THE PREFERRED EMBODIMENTS

Figure 1:
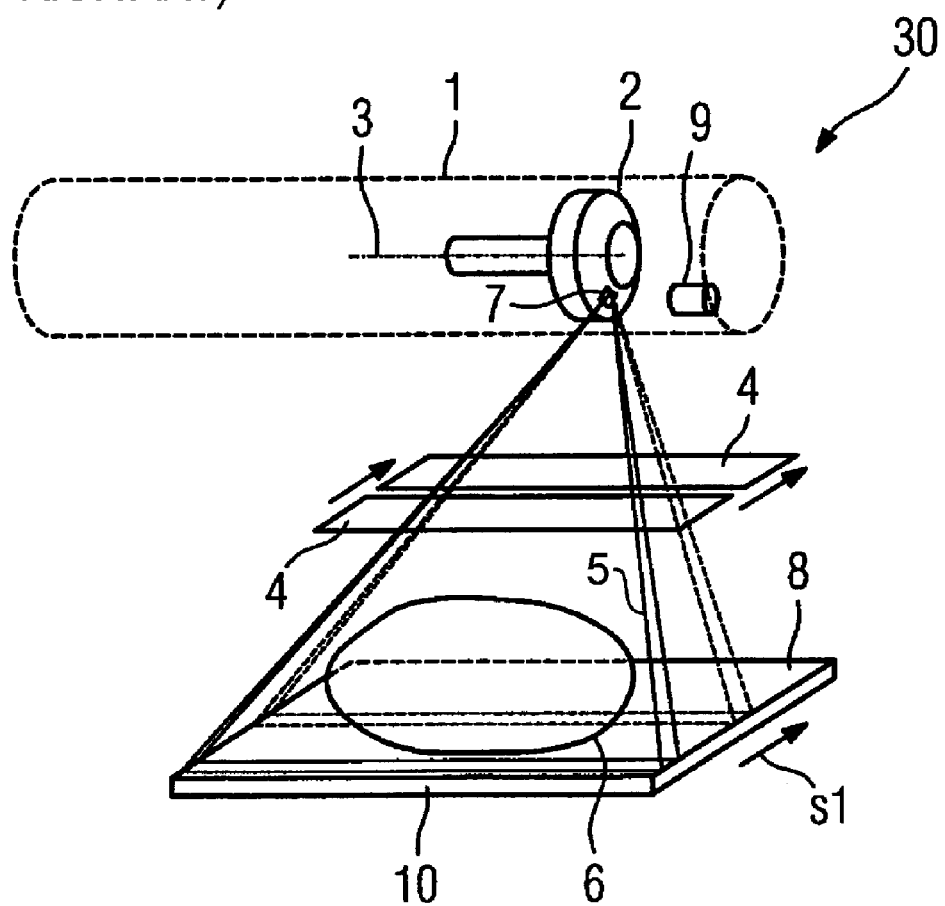
FIG. 1 illustrates a known x-ray device for generation of a scanning movable x-ray beam.

FIG. 1 shows a generally known x-ray device 30 for imaging a subject 6. The device 30 has a slit-shaped diaphragm 4 for generation of a fan-shaped x-ray beam 5 that can be gated from the overall emitted x-ray beam and moved over an examination region 8 in the manner of a scan. The x-ray device 30 has an x-ray tube 1 with a rotary anode 2 that can be rotated around a rotational axis 3, as well as a 2D detector 10 for acquiring the entire examination region of the subject 6. The lengthwise extent of the fan-shaped x-ray beam 5 is essentially parallel to the rotational axis 3 of the rotary anode 2; the scan direction over the examination region is essentially perpendicular to the plane of the fan-shaped x-ray beam 5. The scanning ensues by movement of the opening of the slit-shaped diaphragm 4 in the arrow direction s1.

Figure 2:
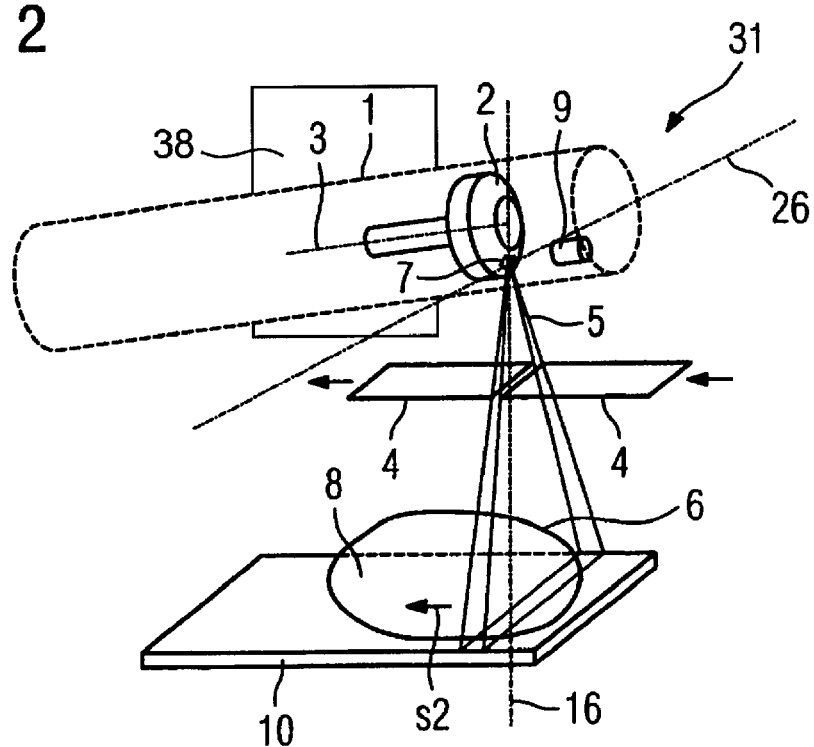
FIG. 2 illustrates an inventive x-ray device in perspective view in a first tilt position.
Figure 3:
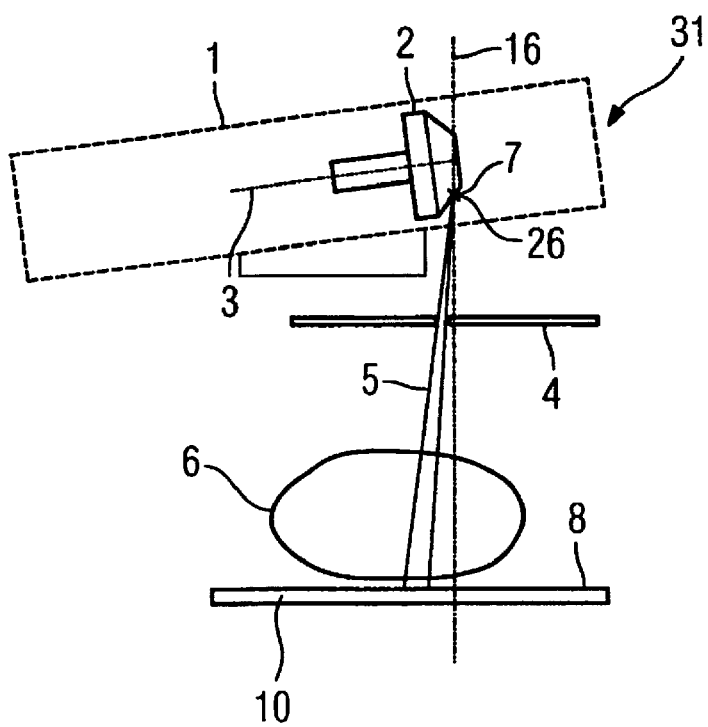
FIG. 3 shows the inventive x-ray device according to FIG. 2 in a side view.
Figure 4:
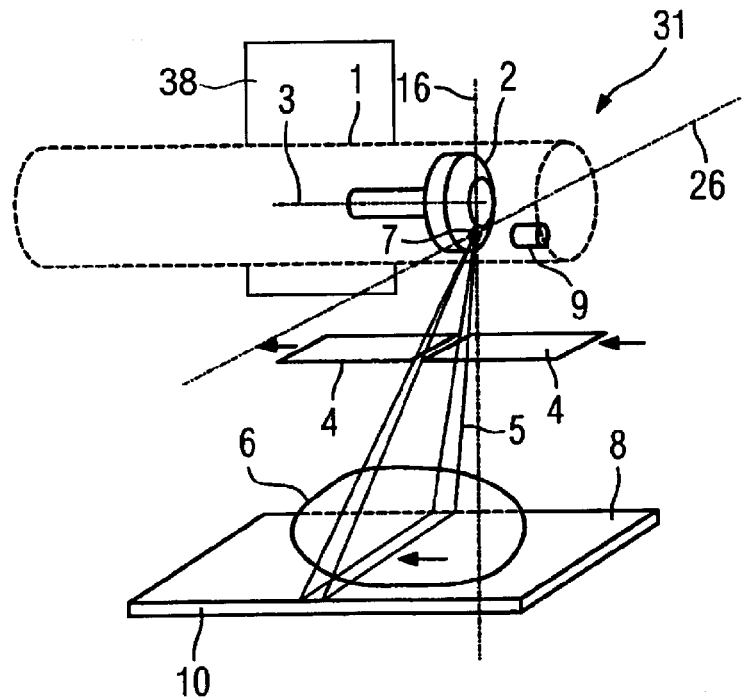
FIG. 4 shows the inventive x-ray device in a perspective view according to FIG. 2 in a second tilt position.
Figure 5:
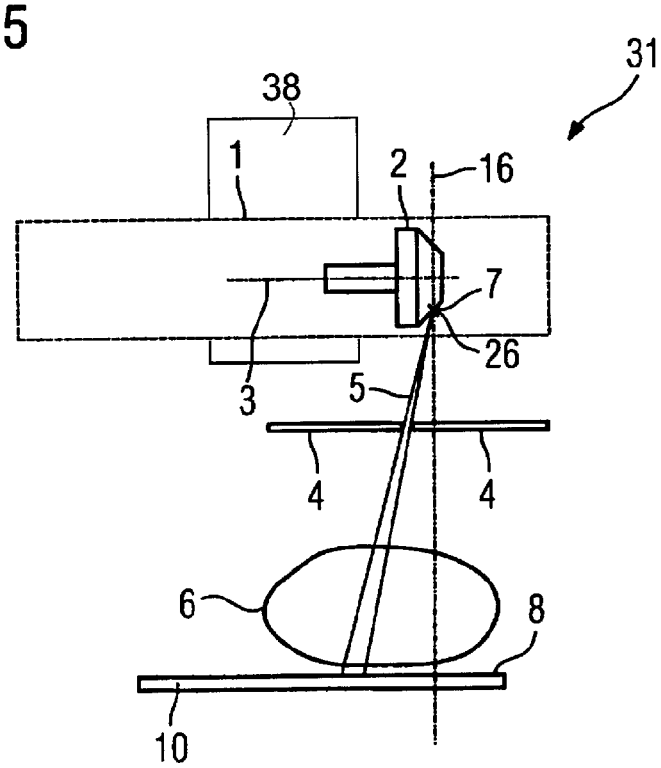
FIG. 5 shows the inventive x-ray device according to FIG. 4 in a side view.
Figure 6:
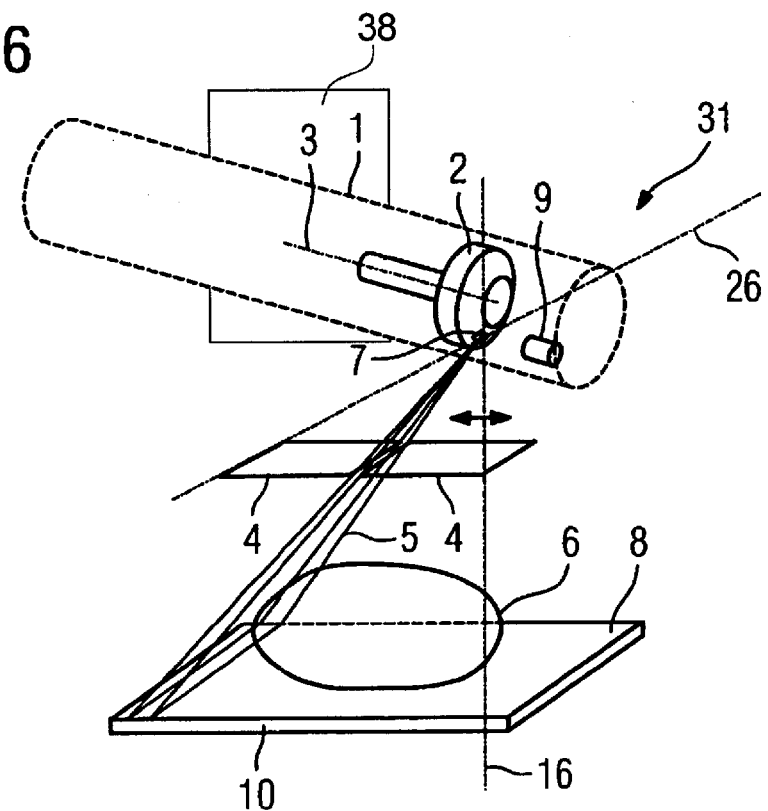
FIG. 6 shows an inventive x-ray device in perspective view in a third tilt position.
Figure 7:
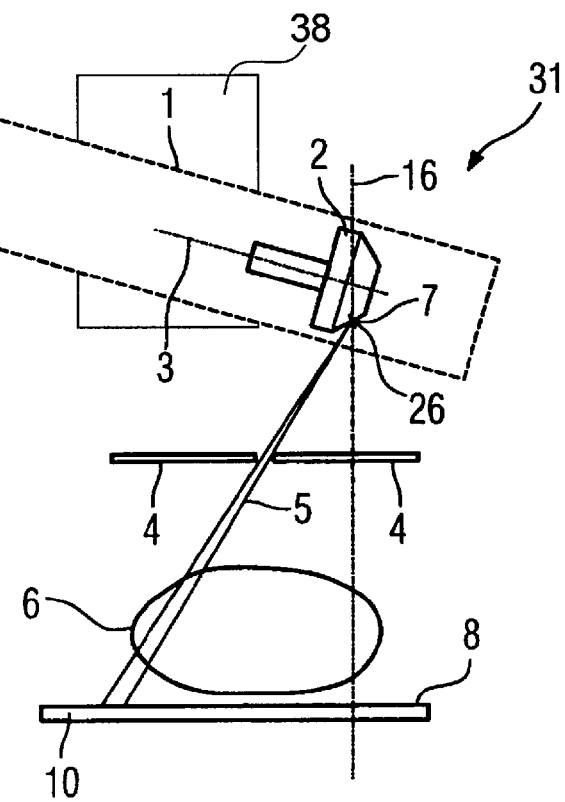
FIG. 7 shows the inventive x-ray device according to FIG. 6 in a side view.

FIG. 2 through FIG. 7 respectively show an inventive x-ray device 31 for scanning a subject 6 on an examination region 8 in various tilt positions of the x-ray tube 1. The x-ray tube 1 emits a total emitted x-ray beam 37 (see FIG. 8). A fan-shaped x-ray beam 5 is gated from the total emitted beam 37 by the slit-shaped diaphragm 4. The total emitted x-ray beam 37 has a region of highest image definition or resolution. The x-ray tube 1 is tiltably mounted at a mounting unit 38 that tilts the x-ray tube 1 to move the fan beam 5 over the examination region 8 in the direction essentially along the rotational axis 3 of the rotary anode 2 and perpendicular to the plane of the fan-shaped x-ray beam 5, as indicated by the arrow s2 on the detector 10 in FIGS. 2, 4 and 6. FIGS. 2 and 3 show a first tilt position of the x-ray tube 2. The tilting by the mounting unit 38 is designed so that the slit-shaped diaphragm 4 always gates in the aforementioned region of the highest image definition of the rotary anode 2 to form the fan beam 5, with a corresponding anode inclination angle that faces the rotary anode 2. The fan-shaped x-ray beam 5 is moved over the examination region 8 in the manner of a scanner by the tilting of the x-ray tube 1 on a tilt axis 26 proceeding through the focal spot 7, parallel to the surface of the examination region 8 and perpendicular to a first axis 16. The diaphragm 4 can be moved as well, synchronized, such that the same x-ray beam 5 remains gated. FIGS. 4 and 5 show a second tilt position of the x-ray tube 1 and FIGS. 6 and 7 show a third tilt position of the x-ray tube 1.

Figure 8:
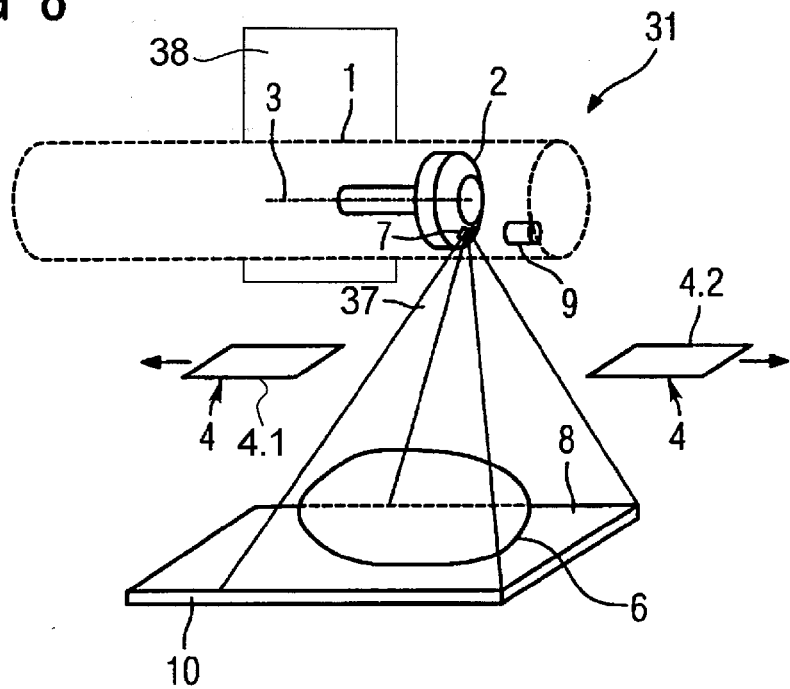
FIG. 8 shows the inventive x-ray device with a diaphragm adjusted for a whole-field image acquisition.

FIG. 8 shows an inventive x-ray device 31 with a slit-shaped diaphragm 4 fashioned with an opening covering the entire examination region. The diaphragm 4 has two diaphragm plates 4.1 and 4.2 delimiting the slit opening that can be moved toward and away from one another and/or relative to one another to displace the slit opening. The inventive x-ray device can also be used in a whole-field mode in a simple manner. This is advantageous since important information can be acquired by comparisons between images of the same subject with the same x-ray device with scatter radiation suppression and without scatter radiation suppression. Moreover, the whole-field mode affords the possibility of using imaging methods that require large fields of view. In the whole-field mode, the inventive tilting of the x-ray tube 1 with the diaphragm 4 moved out of the x-ray beam 5 enables adjustment of the region of highest image resolution of the x-ray beam 5 to each part of the examination region, controlled by the tilting for the particular acquisition.

Moreover, it is possible to move only a single diaphragm plate 4.1 or 4.2 out of the x-ray beam 5 and to use the other diaphragm plate 4.1 or 4.2 to mask partial regions of the x-ray beam 5. The diaphragm plates 4.1 and 4.2 also can be individually or mutually connected to form a unit with the x-ray tube 1 so that they can be tilted as well given a tilting of the x-ray tube 1.

Figure 9:
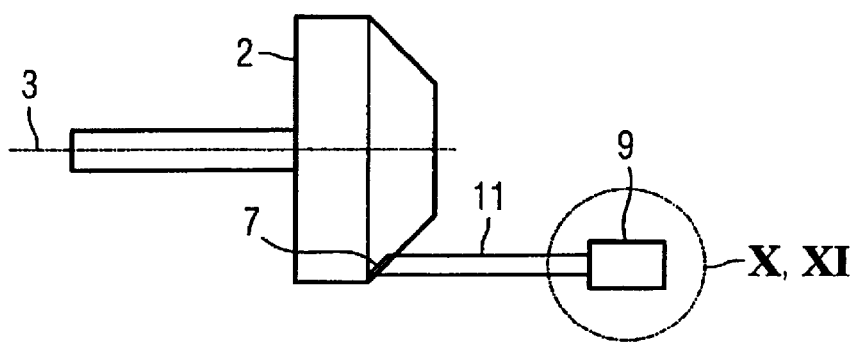
FIG. 9 is a portion of from the x-ray device according to FIG. 2 showing the cathode.
Figure 10:
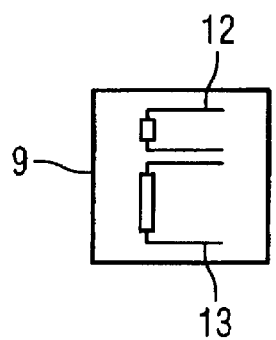
FIG. 10 is a section through the cathode according to FIG. 9.
Figure 11:
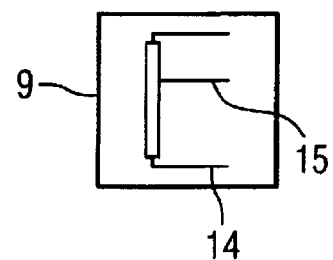
FIG. 11 shows an alternative cathode according to FIG. 9.

FIG. 9 shows a portion of an inventive x-ray device 31 with a rotary anode 2 and a cathode 9 for generation of an electron beam 11 that, through its impact area on the rotary anode 2, determines the size of the focal spot 7. The cathode 9—as shown in FIG. 10—has at least two emitters 12, 13 of different specifications, for generation of focal spots 7 of different dimensions. A selection between at least two differently-sized focal spots is thereby possible. The x-ray power can be increased and thus the scan duration can be reduced by selection of a larger focal spot relative to a smaller one; at the same time losses of image definition can be compensated by the inventive tilting. An alternative cathode 9 is shown in FIG. 11. According to one embodiment of the invention, the cathode 9 has at least one emitter 14 with at least one intermediate tap 15 for separate activation of partial regions of the emitter 14, allowing selection between at least two focal spots of different sizes. Instead of one partial region, the entire emitter 14 can be used for generation of the electron beam and therewith the focal spot 7. An increase of the x-ray power and ultimately a shortening of the scan time thereby result.

A further embodiment of the inventive x-ray device 32 is shown in FIGS. 12 through 13. In addition to the inventive tilting, the x-ray tube 1 also can be rotated in around a first axis 16, proceeding through the focal spot 7 and perpendicular to the examination region 8. FIG. 12 shows the x-ray tube 1 in a first position, for example before rotation around the first axis 16; FIG. 13 shows the same x-ray tube 1 after such a rotation by 90°. A repositioning of the subject 6 is avoided by the rotation. The examination is thereby made easier and less uncomfortable for a patient.

FIG. 14 shows an alternative method for reduction of the scatter radiation in an inventive x-ray device 33. A further movable slit-shaped diaphragm 24 is provided that is arranged proximate to the detector. The detector-proximate diaphragm 24 can be moved over the examination region 8 in synchronization with the x-ray beam 5 such that the scatter radiation is filtered out. The detector-proximate diaphragm 24 alternatively can be fashioned as a scattered-ray grid and be composed of tiltable lamellae diagnosed parallel to the movement direction of the x-ray beam 5. With the use of the detector-proximate diaphragm 24, rotation around the first axis 16 (shown in FIGS. 12 and 13) enables the opening (aperture) of the detector-proximate diaphragm 24 to be moved up to a point directly on the edge of the examination region 8; this was conventionally prevented (for example in mammography) by the sternum of the patient.

In general, in the scanning mode it is also necessary to rotate the diaphragm 24 around the first axis 16. The detector 10 can also be moved at the same time as well. A detector 10 is appropriately fashioned as a detector surface covering the entire examination region 8.

For a further reduction of scatter radiation, in an inventive x-ray device 34 with a detector 19 for conversion of x-ray radiation into an image signal, the detector 19 is designed as a detector row 19 (as is shown, among other things, in FIGS. 15 and 16) covering only a portion of the examination region, extending transverse to the movement direction of the x-ray beam 5 and movable over the examination region 8.

In two views, FIG. 15 and FIG. 16 show a further rotation displacement possibility of the x-ray tube 1. The tiltable x-ray tube 1 can additionally be rotated around a second axis 17 that lies in the plane of the fan-shaped x-ray beam 5, perpendicular to the rotational axis 3 of the rotary anode 2 and outside of the focal spot 7 at the side thereof facing away from the examination region 8. By this rotation around the second axis 17, the fan-shaped x-ray beam 5 can be moved so that the rotational axis 3 of the rotary anode 2 essentially lies in the plane perpendicular to the fan plane of the fan-shaped x-ray beam 5. The focal spot 7, the slit (generated by the slit-shaped diaphragm 4) with its center point and the detector 19 can be appropriately arranged in a line 18 and be moved along this line 18. If, for example, the x-ray tube 1 and the slit-shaped diaphragm 4 are moved together toward the examination region 8, this has the advantage that no distortions of the image can occur. The x-ray power per area can be increased, and therewith the scan time can be reduced, by the approach of the x-ray tube toward the examination region. By rotation of the x-ray tube around the second axis 17 and simultaneous arrangement of the x-ray tube 1, the slit-shaped diaphragm 4 and the detector row 19 in a line 18, the slit-shaped diaphragm 4 and the detector row 19 can be rotated around the second axis 17 in synchronization with the x-ray tube 1, and the examination region 8 can likewise be scanned.

Figure 17:
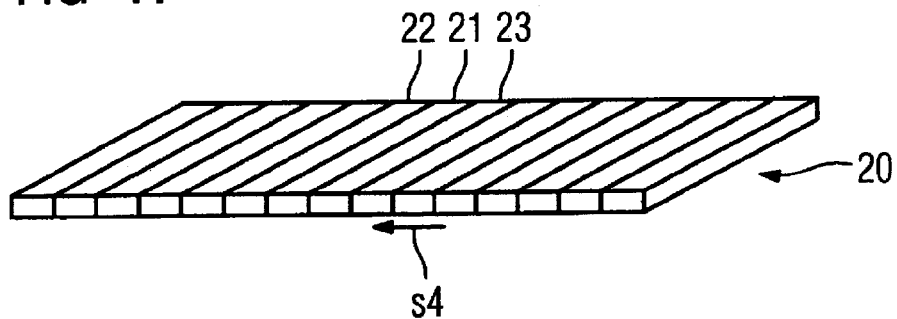
FIG. 17 shows a detector composed of parallel detector rows.

FIG. 17 shows an embodiment with a detector 20 that is composed of a series of parallel detector rows (for example 21-23) arranged perpendicular to the movement direction (indicated by the arrow s4) of the x-ray beam 5.

Figure 18:
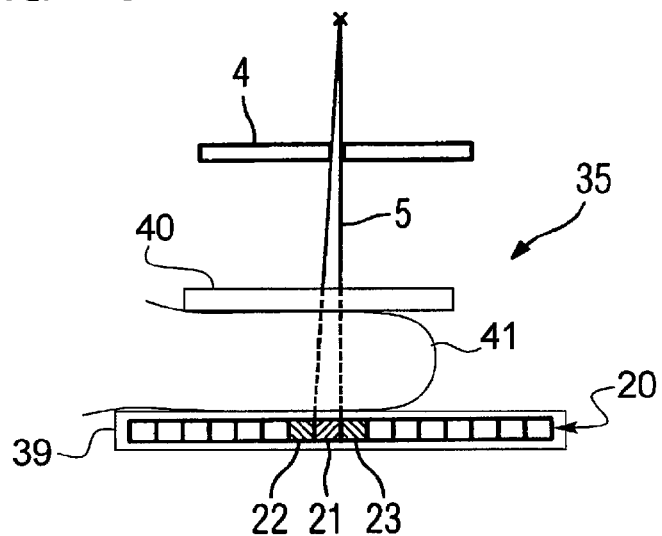
FIG. 18 shows the inventive x-ray device in the embodiment of a mammography apparatus in a side view with individually activatable detector rows.

To prevent scatter radiation, according to one embodiment of the invention the detector rows can respectively be activated individually dependent on being passed over by the x-ray beam 5, as is shown in FIG. 18 wherein the detector row 21 is passed over by the x-ray beam 5. In realization that the scatter radiation can also provide important image information (for example for differential diagnostics) dependent on the subject to be imaged, in an inventive x-ray device 35 detector rows 22; 23 can be activated dependent on the passage of the x-ray beam 5 over adjacent detector row 21 for measurement of scatter radiation. According to one embodiment of the invention, a slit displacement of the slit-shaped diaphragm 4 occurs dependent (in control terms) on changes of the ratio of the scatter radiation to the useable radiation of the ray beam, by widening the opening of the slit-shaped diaphragm 4 upon reduction of the ratio and narrowing the opening of the slit-shaped diaphragm 4 upon an increase of the ratio. Although scatter radiation is low given a very narrow slit, the duration of the scan is long, which can mean an unwanted exposure for the patient.

As also shown in FIG. 18, the x-ray device in accordance with the invention is particularly suited for mammography. FIG. 18 shows a mammography apparatus having a support plate 39 on which a female breast 41 is compressed by a compression plate 40. The radiation detector 20 is disposed in the support plate 39. The support plate 39 and the compression plate 40 as is known, are composed of suitably x-ray transparent material.

According to a further embodiment, in an inventive x-ray device with the dose rate of the x-ray tube dependent on the x-ray beam, a controller for the dose rate of the x-ray tube is provided that controls the dose rate dependent on the image contrast and the radiation exposure of a patient, by increasing of the x-ray dose given low image contrast and reducing the x-ray dose given high radiation exposure of the patient. By the adjustment of the dose in a region passed over at the beginning of the scan, unnecessary radiation exposure of the patient is prevented and, at the same time, the contrast of the x-ray images is optimized for the remaining region.

Figure 19:
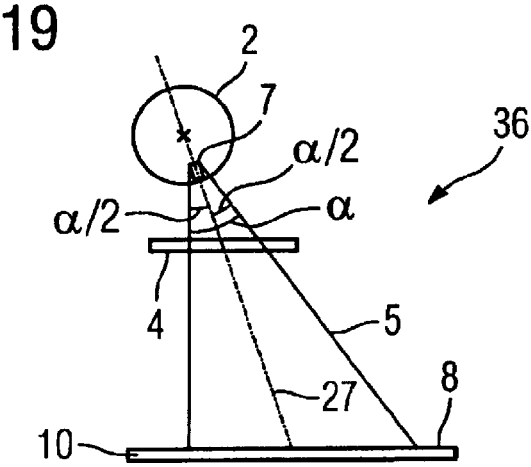
FIG. 19 shows the inventive x-ray examination volume in a frontal plan view with the focal spot positioned in the middle of the aperture angle of the x-ray beam.

FIG. 19 shows a further embodiment of the inventive x-ray device 36. The radial extent of the focal spot 7 is determined by the bisecting lines 27 of the aperture angle α of the x-ray beam 5. The image definition of the x-ray image is thereby additionally increased since this is highest in the plane of the rotary anode at the elongation of the focal spot and is less given removal of this line.

in accordance with the principles of the present invention the image resolution or image definition is improved by fan-shaped ray beam being moved over the examination region essentially in the direction of the rotation axis of the rotary anode and the x-ray tube can be tilted on the focal spot such that the fan-shaped x-ray beam lies in the region of highest image resolution given movement over the examination region.

Although modifications and changes may be suggested by those skilled in the art, it is the intention of the inventors to embody within the patent warranted hereon all changes and modifications as reasonably and properly come within the scope of the contribution to the art.

We claim as our invention:

1. A method for obtaining an x-ray image of a subject, comprising the steps:

irradiating a subject with x-rays produced in an x-ray tube by emitting electrons from a cathode onto a focal spot on a surface of an anode while rotating the anode around a rotation axis to cause an x-ray beam to be emitted from said focal spot, said surface being inclined relative to said rotation axis and thereby causing said x-ray beam to have a varying image resolution/definition within said x-ray beam from a side of said x-ray beam facing said cathode to a side of said x-ray beam facing said anode, with an x-ray beam of highest image resolution/definition being at said side of said x-ray beam facing said anode;

gating said x-ray beam to produce a fan-shaped x-ray beam therefrom;

moving said fan-shaped x-ray beam through an examination region, containing said subject, substantially in a direction of the rotation axis of said rotary anode by tilting said x-ray tube relative to said focal spot to cause said fan-shaped x-ray beam to always to be gated from said region of highest image resolution/definition during movement of said fan-shaped x-ray beam through the examination region; and detecting x-rays in said fan-shaped x-ray beam attenuated by said subject and generating an x-ray image of the subject therefrom.

2. A method as claimed in claim 1 comprising gating said x-ray beam with a slit-shaped diaphragm to produce said fan-shaped x-ray beam, and displacing said slit-shaped diaphragm through said examination region in said direction of said rotation axis synchronized with the movement of the fan-shaped x-ray beam through the examination region.

3. A method as claimed in claim 1 comprising gating said x-ray beam with a slit-shaped diaphragm having a displaceable opening therein to produce said fan-shaped x-ray beam, and displacing said opening within said slit-shaped diaphragm in said direction of said rotation axis synchronized with the movement of the fan-shaped x-ray beam through the examination region.

4. A method as claimed in claim 1 wherein said rotary anode has a radial direction associated therewith, and comprising controlling operation of said cathode to selectively enlarge a cross-section of said electron beam to enlarge said focal spot in said radial direction.

5. A method as claimed in claim 1 comprising rotating said x-ray tube around an axis proceeding through said focal spot and perpendicular to said examination region while moving said fan-shaped x-ray beam through said examination region.

6. A method as claimed in claim 5 wherein said axis is a first axis, and additionally rotating said x-ray tube around a second axis disposed in a plane of said fan-shaped x-ray beam and being perpendicular to said rotation axis, said second axis being disposed outside of said focal spot at a side of said focal spot facing away from said examination region.

7. A method as claimed in claim 1 comprising detecting said fan-shaped x-ray beam attenuated by said subject using a radiation detector comprising a detector row extending through only a portion of said examination region transverse to a direction of movement of said fan-shaped x-ray beam through said examination region, by electronically moving said detector row through said examination region.

8. A method as claimed in claim 7 comprising gating said x-ray beam with a slit-shaped diaphragm having a slit-opening with a center point to produce said fan-shaped x-ray beam, and wherein said detector row has a center point, and orienting said x-ray tube, said slit-shaped diaphragm and said detector row relative to each other to place said focal spot, said center point of said opening and said center point of said row detector on a straight line that is moveable through said examination region.

9. A method as claimed in claim 1 comprising gating said x-ray beam with a first slit-shaped diaphragm to produce said fan-shaped x-ray beam before said fan-shaped x-ray beam passes through said examination region, and detecting said fan-shaped x-ray beam attenuated by said subject with a radiation detector, and gating said fan-shaped x-ray beam with a second slit-shaped diaphragm disposed approximate said radiation detector, and moving said second slit-shaped diaphragm through said examination region in said direction of said rotation axis synchronized with the movement of said fan-shaped x-ray beam through said examination region.

10. A method as claimed in claim 1 comprising gating said x-ray beam with a slit-shaped diaphragm, comprising two diaphragm plates disposed opposite each other that define an opening that gates said x-ray beam, to produce said fan-shaped x-ray beam, and selectively moving said diaphragm plates toward and away from each other to selectively define a width of said opening, and thus a width of said fan-shaped x-ray beam.

11. A method as claimed in claim 10 comprising detecting said fan-shaped x-ray beam attenuated by said subject using a radiation detector and, in said radiation detector, converting the attenuated x-rays into an electrical image signal, and also detecting scatter radiation, associated with said fan-shaped x-ray beam, with said radiation detector, and automatically determining a ratio of said scatter radiation to radiation converted into said electrical image signal and controlling displacement of said diaphragm plates relative to each other to widen said opening as said ratio decreases and to narrow said opening as said ratio increases.

12. A method as claimed in claim 1 wherein said fan-shaped x-ray beam has a dose rate associated therewith, and comprising automatically calculating a radiation exposure to the subject in said examination region from said dose rate and comprising detecting said fan-shaped x-ray beam attenuated by said subject with a radiation detector and, in said radiation detector, converting the attenuated radiation into an electronic image signal representing an image having an image contrast associated therewith, and automatically controlling said dose rate dependent on said radiation exposure and said image contrast to increase said dose rate upon a low image contrast and to decrease said dose rate upon a high radiation exposure.

13. A method as claimed in claim 1 wherein said subject is a female breast, and comprising detecting said fan-shaped x-ray beam attenuated by said female breast using a radiation detector disposed in a support plate, and compressing said female breast between said support plate and a compression plate disposed above said support plate while moving said fan-shaped x-ray beam through said examination region.

* * * * *